United States Patent [19]

Womack

[11] 4,416,664
[45] Nov. 22, 1983

[54] CATHETER SECURING DEVICE

[76] Inventor: Charles E. Womack, 2122 Helton Dr., Florence, Ala. 35630

[21] Appl. No.: 301,451

[22] Filed: Sep. 11, 1981

[51] Int. Cl.³ .............................................. A61M 5/32
[52] U.S. Cl. ...................................... 604/174; 604/179
[58] Field of Search .................. 128/133, 295, 214 R, 128/DIG. 26, 349 R (U.S. only), 85, 80 G; 24/164, 182; 604/175, 179, 180

[56] References Cited

U.S. PATENT DOCUMENTS

| | | | |
|---|---|---|---|
| 3,812,851 | 5/1974 | Rodriguez | 604/179 |
| 4,096,863 | 6/1978 | Kaplan et al. | 128/349 R |
| 4,249,529 | 2/1981 | Nestor | 128/DIG. 26 |
| 4,294,238 | 10/1981 | Woodford | 128/80 G |
| 4,316,461 | 2/1982 | Marais et al. | 128/214 R |
| 4,333,468 | 6/1982 | Geist | 128/DIG. 26 |

*Primary Examiner*—C. Fred Rosenbaum
*Assistant Examiner*—J. L. Kruter
*Attorney, Agent, or Firm*—Woodford R. Thompson, Jr.

[57] ABSTRACT

A catheter securing device embodies a supporting pad-like member having a first flexible strap extending laterally therefrom to encircle a leg of a person. Cooperating fastener members are carried by facing surfaces of the strap when encircling the leg to detachably connect the pad-like member about the leg. An elongated resilient gripping member is carried by the pad-like member in position to at least partially encircle the catheter tube and restrain movement thereof relative to the pad-like member. A second flexible strap is carried by the pad-like member adjacent one side of the gripping member and is adapted to extend over the gripping member and engage a retainer element carried by the pad-like member adjacent the other side of the gripping member. Connector elements carried by the second strap engage adjacent fastener members carried by the first flexible strap to retain the catheter within the gripping member.

4 Claims, 10 Drawing Figures

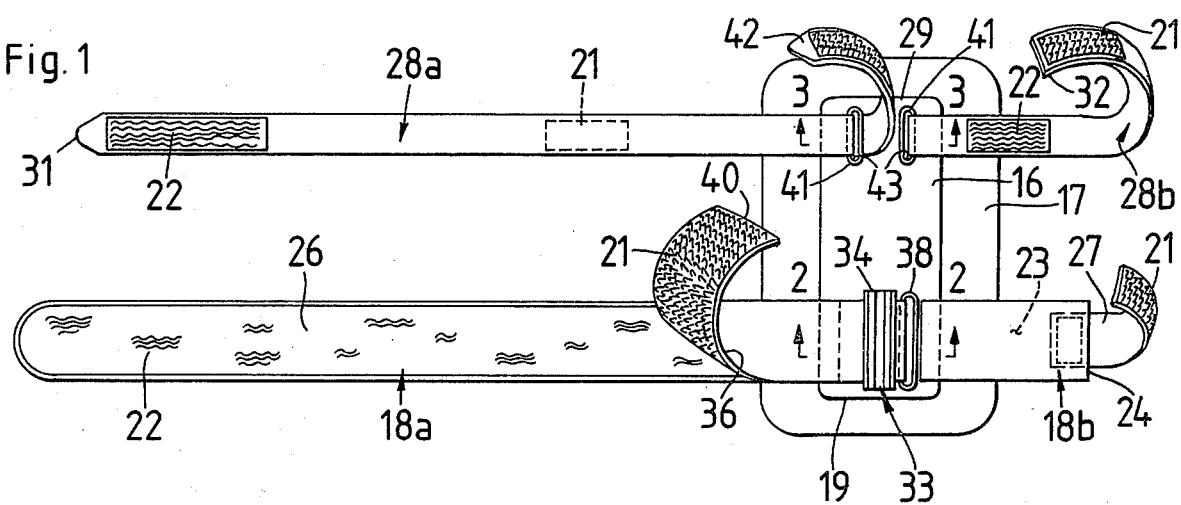
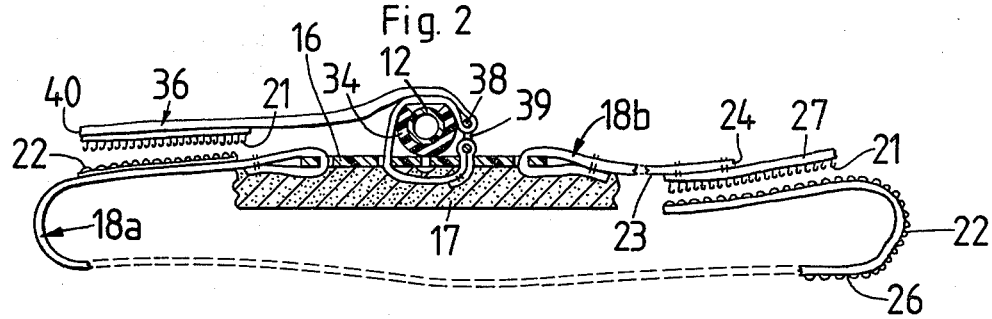
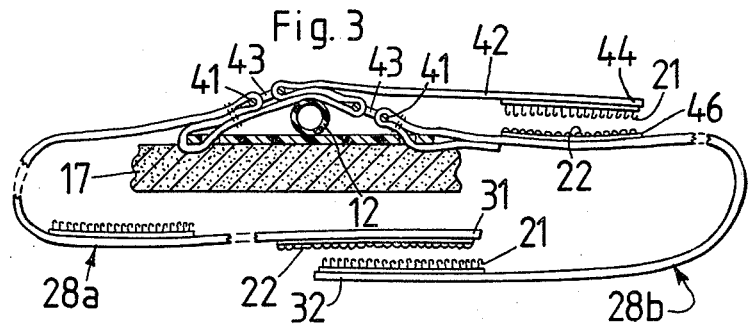
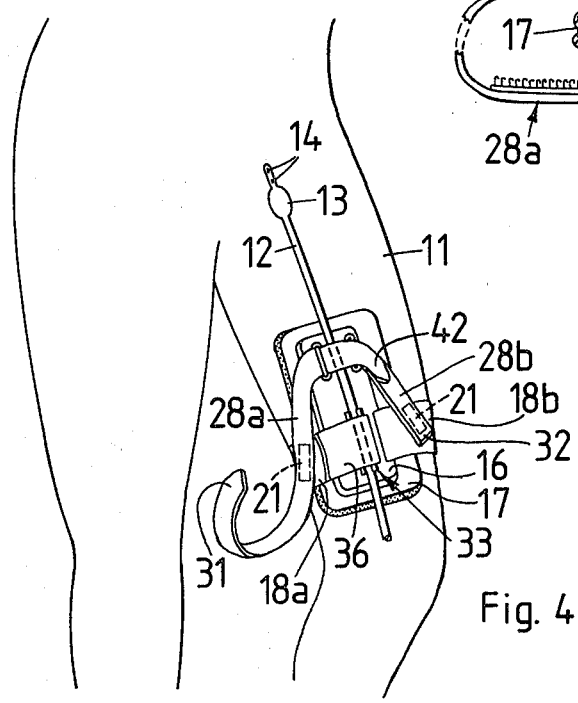
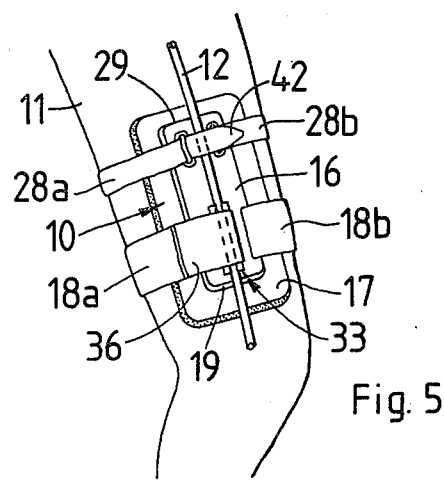

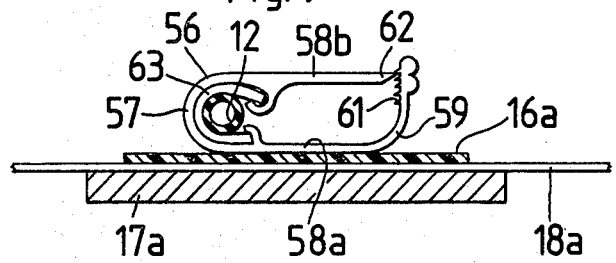
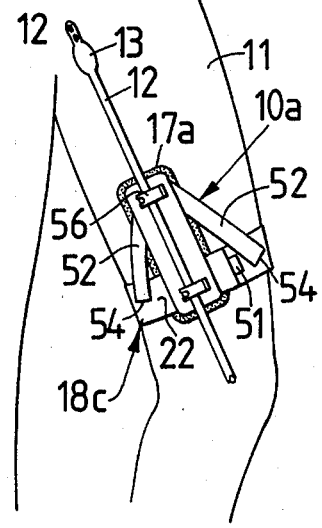
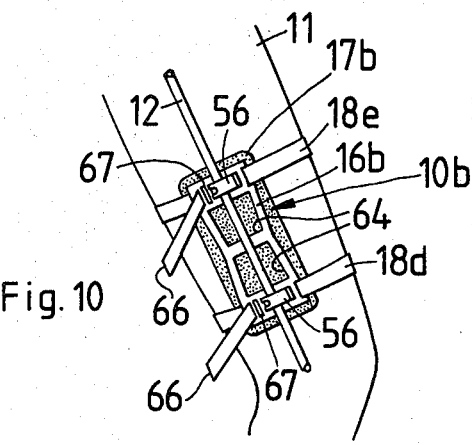
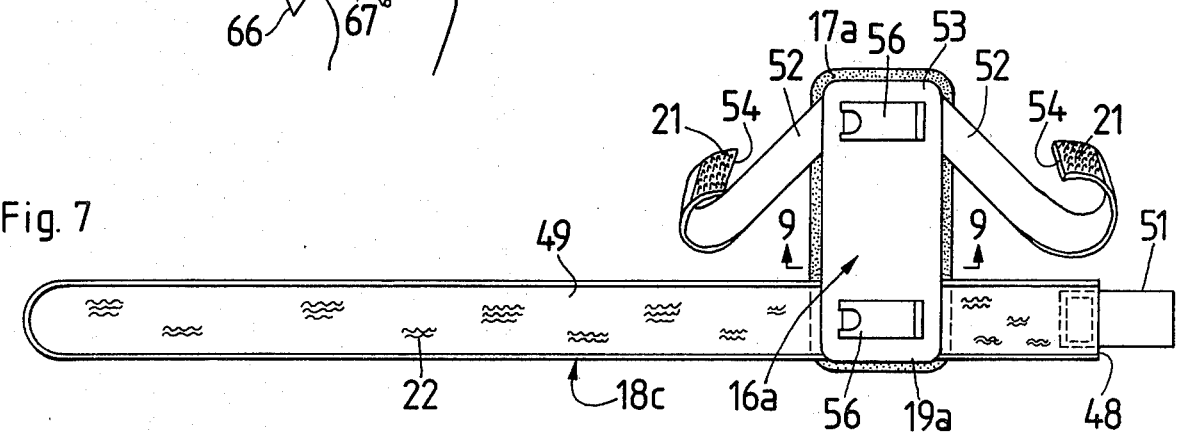
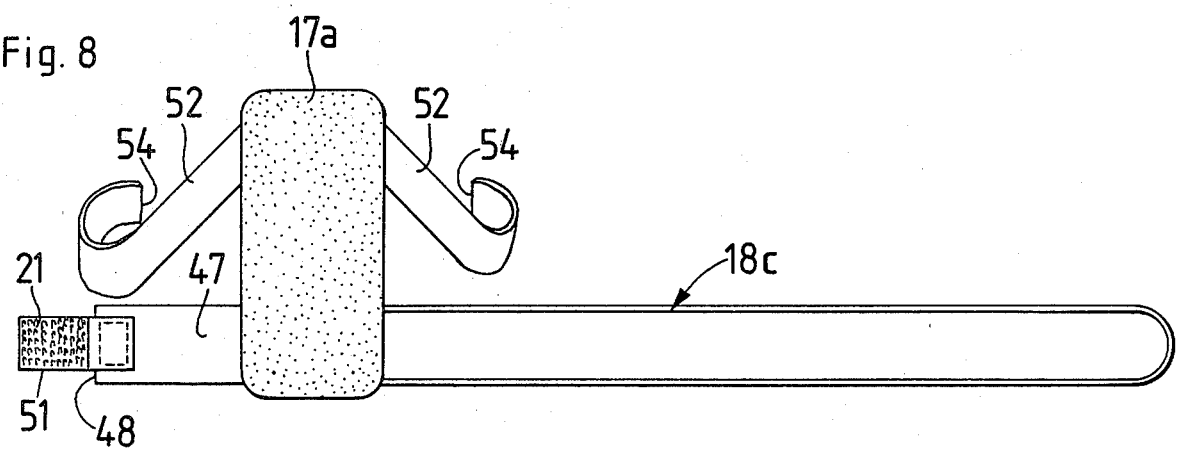

CATHETER SECURING DEVICE

BACKGROUND OF THE INVENTION

This invention relates to a device for securing an indwelling Foley catheter to a limb of a person and more particularly to a device which is particularly useful with postoperative male patients who have had a transurethal resection of the prostate gland or an open prostatectomy where some degree of catheter traction may be desired.

Heretofore in the art to which my invention relates there has been a great need for a better and more practical means for securing Foley catheters left indwelling and for improving patient comfort while at the same time providing catheter stability. A need has also existed for a device which would secure the Foley catheter under traction following prostatic surgery to obtain tamponade and thereby decrease postoperative bleeding. Many male patients who have undergone surgery transurethrally for prostate gland obstruction or who have had an open surgical procedure for the same problem (open prostatectomy) have postoperative bleeding from the surgical site. One method of decreasing this postoperative bleeding is to insert a Foley catheter into the bladder, inflate the catheter balloon and pull the catheter balloon down against the bladder neck, thus tamponading the bleeding which is present. The Foley catheter tubing oftentimes must be placed under traction to obtain and maintain the tamponade effect. Current methods of obtaining this catheter traction include: (1) shaving the thigh and taping the catheter with traction to the leg. This method of obtaining traction is not satisfactory in that, invariably, skin abrasions and blisters result due to the traction and tension exerted against the skin of the leg. (2) Use of conventional leg straps with which I am familiar serve a useful function but none provide proper catheter traction without slipping on the leg or constricting the leg where sufficient tension is exerted to provide adequate traction on the catheter. The flow of urine and irrigating solution through the catheter may also be impaired if too much tension is applied to the catheter to secure it. Conventional leg straps with which I am familiar are disclosed in the following U.S. Pat.: Nos. 3,726,280; 3,765,421; 3,878,849; and 4,096,863.

SUMMARY OF THE INVENTION

In accordance with my invention, I overcome the above and other difficulties by providing a catheter securing device which is simple of construction, economical of manufacture and one which is dependable and provides maximum comfort to the patient.

It is an object of my invention to provide a catheter securing device which may be detachably connected to different size limbs in a manner which positively restrains slippage on the limb to which it is attached, thus significantly reducing irritation to the bladder and discomfort to the patient as the patient moves about.

Another object of my invention is to provide a device which maintains a catheter in traction about the leg of a person in a manner which produces a tamponade effect by retaining the inflated catheter balloon in a downward position against the bladder neck thereby decreasing postoperative bleeding.

A further object of my invention is to provide a catheter securing device which may be easily assembled and adjusted on a patient's leg without impairing the flow of urine and/or irrigating solution through the catheter tube.

A still further object is to provide a catheter securing device which eliminates the use of tape which results in burns and skin blisters that form on the patient's leg.

Yet another object of my invention is to provide a securing device for a catheter tube which permits visual inspection of the tube while in use.

Yet another object of my invention is to provide immobility of the catheter tube and drainage tubing when no traction on the catheter is desired, thereby improving the comfort to the patient and positively securing the catheter in position.

My improved catheter securing device embodies a supporting pad-like member adapted to extend alongside and contact the leg of a person. At least one flexible strap is carried by the pad-like member for encircling the leg of the person. Cooperating fastener members carried by facing surfaces of the strap when encircling the leg of the person detachably connect the pad-like member to the leg. An elongated resilient gripping member is carried by the pad-like member in position to encircle the catheter tube and restrain movement thereof relative to the pad-like member. A flexible secondary strap is secured to the pad-like member adjacent one side of the gripping member. The secondary strap is adapted to extend over the gripping member and engage a retainer element carried by the pad-like member adjacent the other side of the gripping member. Connector elements carried by the secondary strap engage adjacent fastener members carried by the flexible strap to retain the catheter within the gripping member.

DESCRIPTION OF THE DRAWINGS

Apparatus embodying features of my invention is illustrated in the accompanying drawings, forming a part of this application, in which:

FIG. 1 is a top plan view showing my improved catheter securing device removed from the person's leg and with the straps extending therefrom in a single plane for clarity;

FIG. 2 is an enlarged sectional view taken along the line 2—2 of FIG. 1;

FIG. 3 is an enlarged sectional view taken along the line 3—3 of FIG. 1;

FIG. 4 is a view showing one flexible strap extending around and detachably connecting my securing device about the leg of a person;

FIG. 5 is a view corresponding to FIG. 4 showing additional flexible straps extending around the leg of the person;

FIG. 6 is a view showing a modified form of my improved catheter securing device detachably connected about the leg of a person;

FIG. 7 is an enlarged top plan view of the device shown in FIG. 6 removed from the person's leg for clarity;

FIG. 8 is a bottom view of the catheter securing device shown in FIG. 7;

FIG. 9 is an enlarged sectional view taken generally along the line 9—9 of FIG. 7; and FIG. 10 is a view showing another modified form of my improved catheter securing device.

DETAILED DESCRIPTION

Referring now to the drawings for a better understanding of my invention, I show in FIGS. 4 and 5 my improved catheter securing device 10 detachably connected about the leg 11 of a person. The device 10 is detachably connected to a catheter tube 12 having an upper end portion adapted to be inserted into a person's bladder. A catheter balloon 13 carried by the upper end portion of the tube 12 is inflatable after insertion inside the person's bladder. The tube 12 is divided into three separate passageways, one of which is utilized to inflate the catheter balloon 13. The second passageway drains fluids from the bladder and is connected to one opening of a pair of openings 14 provided adjacent the catheter balloon 13, as shown. The third passageway provides means for introducing fluid into the bladder through the other opening 14.

My improved catheter securing device 10 embodies a supporting pad-like member 16 which may be in the form of a rigid or semi-rigid member formed from a suitable plastic-like material and adapted to extend alongside the leg of the person, as shown. Forming a part of the pad-like member 16 is a resilient backing member 17 which is formed of a suitable material, such as foam rubber, and is carried by the surface of the pad-like member 16 adjacent the leg 11. The foam rubber backing member 17 provides a comfortable surface for contacting the leg 11 and also aids in retaining the pad-like member 16 in place on the leg.

As shown in FIGS. 1, 4 and 5, flexible straps 18a and 18b are carried by and extend laterally from one end portion 19 of the pad-like member 16 in position to encircle the leg 11 and detachably connect the pad-like member 16 thereto. Preferably the pad-like member 16 extends generally perpendicular to the straps 18a and 18b whereby the device 10 is adapted to be detachably connected about either leg of the person. However, it will be apparent that the pad-like member 16 may be secured at other angles relative to the straps 18a and 18b whereby the device 10 may be particularly adapted for use with only one leg of the person.

As shown in FIG. 2, cooperating fastener members are carried by facing surfaces of the straps 18a and 18b when encircling the leg of the person. That is, a multiplicity of connector elements, such as hook-like members 21, are carried by one of the facing surfaces in position to detachably engage a felt-like material 22 carried by the other facing surface. Preferably, the hook-like members 21 are carried by one side 23 of the strap 18b adjacent one end portion 24 thereof, with the felt-like material 22 being carried by the adjacent side 26 of the strap 18a. While I have shown the hook-like members 21 as being carried by a separate member 27 secured to the end portion 24 of the strap 18b, it will be apparent that the hook-like members may be secured directly to the side 23 adjacent the end portion 24. The felt-like material 22 extends substantially the entire length of the outer surface of the strap 18a while encircling the leg 11 whereby the device 10 may be detachably connected to limbs of various sizes. A conventional type fastening device embodying such hook-like members 21 and felt-like material is sold under the trade name "VELCRO". While I have shown the straps 18a and 18b as being separate straps carried by the end portion 19 of the pad-like member 16, it will be apparent that a single strap may be carried by the end portion 19 for detachably connecting the device 10 about the person's leg.

As shown in FIGS. 1 and 5, a pair of additional flexible straps 28a and 28b extend laterally from the other end portion 29 of the pad-like member 16. The straps 28a and 28b are adapted to encircle the person's leg and detachably connect the pad-like member 16 thereto. As shown in FIG. 3 connector members, such as the hook-like members 21 and the felt-like material 22, are carried by facing end portions 31 and 32 of the straps 28a and 28b, respectively, when encircling and connecting the pad-like member 16 to the patient's leg 11. This assembly of the straps 28a and 28b is particularly useful with nursing home patients who require prolonged catheter drainage without the catheter tubing being placed under traction.

In FIG. 4 I show the additional straps 28a and 28b extending diagonally from the end portion 29 of the pad-like member 16 toward the straps 18a and 18b. A plurality of hook-like members 21 are carried by the additional strap 28a intermediate its ends thereof in position to engage the felt-like material 22 carried by the outer surface of the strap 18a, as shown. This assembly is particularly useful when catheter traction is desired as is the case with male patients who have had an open prostatectomy where tamponading of the bleeding from the surgical site is required. In this assembly, the straps 28a and 28b are adapted to engage the felt-like material 22 at selected positions along the strap 18a. Accordingly, the pull exerted against the device 10 by the catheter tube 12 as the patient moves about is more evenly distributed about the strap 18a instead of being concentrated at a single point. Also, the distribution of the pull about the strap 18a permits the device 10 to be detachably connected about the leg with less gripping force than required with conventional leg straps. Accordingly, constriction of the leg is significantly reduced.

A catheter tube securing member, indicated generally at 33, is carried by the end portion 19 of the pad-like member 16 for detachably connecting it to the catheter tube 12, as shown in FIGS. 1 and 2. The securing member 33 embodies an elongated, resilient catheter gripping member 34 which may be formed from an elastic rubber-like material and is adapted to at least partially encircle the catheter tube 12 and restrain movement thereof relative to the pad-like member 16. A flexible secondary strap 36 of a length less than the length of the flexible strap 18a is secured to the pad-like member 16 adjacent one longitudinal side of the gripping member 34, as shown in FIG. 2. A retainer member 38, such as a conventional clip-like member is carried by the pad-like member 16 at the point of attachment of the secondary strap 36. As shown in FIG. 2, the retainer member 38 is provided with an elongated opening 39 therebetween for receiving the free end portion 40 of the secondary strap 36 after it extends over the gripping member 34. Connector members, such as hook-like members 21, are carried by the end portion 40 of the secondary strap 36 for detachably connecting it to the felt-like material 22 carried by the outer surface of the strap 18a whereby the catheter tube 12 is retained within the gripping member 34.

In FIG. 3 I show a pair of spaced apart retainer elements 41 and another flexible secondary strap 42 detachably connecting the catheter tube 12 to the end portion 29 of the pad-like member 16. The retainer elements 41, which may also be in the form of elongated clip-like members, are carried by the pad-like member 16 in spaced relation to each other to provide clearance for the catheter tube 12 to extend therebetween. The flexible secondary strap 42 is secured to the pad-like member 16 and is adapted to extend over the catheter tube 12 and through an elongated opening 43 provided in each retainer element 41, as shown. Hook-like members 21 are also carried by the free end portion 44 of the strap 42 for detachably connecting the strap 42 to a strip 46 of felt-like material 22 carried by an intermediate portion of the strap 28b, as shown.

From the foregoing description, the operation of my improved catheter securing device will be readily understood. The upper end of the catheter tube 12 carrying the catheter balloon 13 is inserted into the patient's bladder and the catheter balloon 13 is inflated. The catheter securing device is detachably connected about the patient's leg 11 so that the balloon 13 is retained in a downward position against the neck of the bladder. The elongated gripping member 34 and the secondary strap 42 detachably connect the catheter tube 12 to the pad-like member 16. If traction is not required, the additional straps 28a and 28b may be detachably connected about the patient's leg, as shown in FIG. 5. If catheter traction is required, as is the case with male patients who have had an open prostatectomy, the straps 28a and 28b are detachably connected to the straps 18a and 18b, as shown in FIG. 4. The constant pressure exerted by the balloon 13 against the bladder neck will thus tamponade the bleeding in the bladder. Also, fluids may be easily introduced and drained from the bladder and at the same time the patient experiences less discomfort as he moves about.

Referring now to FIGS. 6-9, I show a modified from of my catheter securing device at 10a which is particularly adapted for use where catheter traction is required. The securing device 10a comprises a supporting pad-like member 16a, which may be formed of a suitable plastic-like material, and is adapted to extend alongside the patient's leg 11. A resilient backing member 17a formed of a suitable foam rubber-like material is carried by the surface of the pad-like member 16a adjacent the leg of the patient. A flexible strap 18c extends laterally from one end portion 19a of the pad-like member 16a in position to encircle and detachably connect the pad-like member to the patient's leg 11. Preferably the pad-like member 16a extends generally perpendicular to the strap 18c so that the device 10a is adapted to be detachably connected about either leg of the patient. However, it will be apparent that the pad-like member 16a may be secured at other angles relative to the strap 18c whereby the device 10a will be particularly adapted for use with only one leg of the patient.

As shown in FIGS. 7 and 8, cooperating fastener members, such as the hook-like members 21 and the felt material 22, are carried by facing surfaces of the strap 18c while it encircles the leg 11 of the person. Preferably, the hook-like members 21 are carried by one side 47 of the strap 18c adjacent one end portion 48 thereof, with the felt-like material 22 being carried by the opposite side 49 thereof. While I have shown the hook-like members 21 as being carried by a separate member 51, it will be apparent that they may be secured directly to the end portion 48. The felt-like material 22 carried by the strap 18c extends substantially the entire length of the strap 18c whereby the device 10a may be detachably connected about limbs of various sizes.

As shown in FIGS. 6, 7 and 8, a pair of additional flexible straps 52 extend diagonally from the other end portion 53 of the pad-like member 16a toward the strap 18c. Connector members, such as hook-like members 21, are carried by end portions 54 of the additional straps 52 for engaging felt-like material 22 carried by the strap 18c. The additional straps 52 are thus adapted to engage the felt-like material 22 at selected positions along the strap 18c. Accordingly, any pull exerted by the device 10a is more evenly distributed about the strap 18c and permits the device 10a to be detachably connected about the patient's leg with less gripping force than heretofore required.

As shown in FIGS. 6, 7 and 9, a pair of spaced apart clamping members 56 are carried by the outer surface of the pad-like member 16a for detachably connecting the catheter tube 12 thereto. Each clamping member 56 embodies a generally U-shaped member having a curved base portion 57 with a pair of spaced apart legs 58a and 58b connected thereto. The leg 58a extends alongside and is secured to the outer surfaces of the pad-like member 16a by suitable means, as shown. A laterally extending curved member 59 having serrations 61 thereon is carried by the leg 58a, as shown. The leg 58b extends outwardly from the curved base portion 57 and terminates in a free portion 62 which is adapted to engage selected ones of the serrations 61 carried by the leg 58a. A resilient gripping member 63, which may be formed from an elastic rubber-like material, extends alongside the inner surface of the curved base portion 57 in position to engage and restrain movement of the catheter tube 12. Each clamping member 56 permits visual inspection of the catheter tube 12 while it is in a locked position extending through the device 10a, as shown. Also, each clamping member 56 is adapted to receive catheter tubes of various diameters and retain them in place without crimping them or restraining the flow of urine and/or irrigating solutions therethrough.

From the foregoing description, the operation of my improved catheter securing device 10a will be readily understood. The upper end of the catheter tube 12 carrying the catheter balloon 13 is inserted into the patient's bladder and the catheter balloon 13 is inflated. The securing device 10a is detachably connected about the leg 11 so that the catheter balloon 13 is retained in a downward position against the neck of the bladder while the catheter tube 12 is secured under traction by the clamping members 56, as shown. The constant pressure exerted by the balloon 13 against the bladder neck will thus tamponade the bleeding in the bladder. Also, fluids may be easily introduced and drained from the bladder while the patient experiences considerably less discomfort while moving about.

Referring now to FIG. 10, I show another modified form of my improved catheter securing device at 10b which is particularly adapted for use with patients wearing catheters for an extended period of time whereby the patient may walk and move about rather extensively. That is, the catheter tube 12 must be stabilized during such extensive movement and at the same time it should be detachably connected to a securing device which is comfortable to the patient.

The modified form of my improved catheter securing device shown in FIG. 10 comprises a supporting pad-like member 16b such as a semi-rigid member formed of a suitable plastic-like material, which is adapted to extend alongside the leg of a person. Openings 64 may be provided in the pad-like member 16b to aid in making it flexible and more comfortable for the patient to wear. A resilient backing member 17b, formed of a suitable material such as foam rubber, is carried by the surface of the pad-like member 16b adjacent the leg of the patient. Flexible straps 18d and 18e are carried by the pad-like member 16b and extend laterally from each end thereof.

The straps 18d and 18e are of a sufficient length to encircle and detachably connect the pad-like member 16b to limbs of various sizes. The free end 66 of each strap 18d and 18e is adapted to be connected to a buckle-type connection 67 carried by the pad-like member 16b to thus detachably connect the pad-like member about the leg of the patient. Also, clamping members 56 are carried by the pad-like member 16d to detachably connect the catheter tube 12 thereto.

From the foregoing, the operation of my improved catheter securing device 10b will be readily understood. With the upper end of the catheter tube 12 inserted in the patient's bladder and the catheter balloon 13 inflated, as described above, the device 10b is detachably connected about the patient's leg. The balloon 13 is retained in a downward position against the neck of the bladder by the attachment of catheter tube 12 to the device 10b, as shown in FIG. 10.

From the foregoing it will be seen that I have devised an improved catheter securing device which is simple of construction and economical of manufacture. Also, my improved device may be easily and quickly attached to different size limbs in a manner which positively prevents slippage on the limb and at the same time it is comfortable to wear since it reduces significantly constriction of the limb to which it is attached.

While I have shown my invention in several forms, it will be obvious to those skilled in the art that it is not so limited, but is susceptible of various other changes and modifications without departing from the spirit thereof.

What I claim is:

1. A device for securing a catheter or the like to a leg of a person comprising:
   (a) a supporting pad-like member adapted to extend alongside and contact said leg of a person,
   (b) at least one flexible strap secured to said pad-like member adjacent one end portion thereof and extending laterally therefrom in position to encircle said leg of the person,
   (c) means detachably connecting said strap about said leg of the person,
   (d) means carried by said pad-like member for detachably connecting a catheter thereto and restraining longitudinal movement thereto, and
   (e) a pair of additional flexible straps secured to and extending diagonally from the other end portion of said pad-like member toward said one flexible strap with connector means detachably connecting end portions of said additional flexible straps to the outer surface of said one flexible strap.

2. A device for securing a catheter or the like to a leg of a person comprising:
   (a) a supporting pad-like member adapted to extend alongside and contact said leg of a person,
   (b) at least one flexible strap carried by said pad-like member and extending laterally therefrom in position to encircle said leg of the person,
   (c) means detachably connecting said strap about said leg of the person,
   (d) an elongated resilient catheter gripping member carried by said pad-like member and adapted to at least partially encircle said catheter to restrain movement thereof relative to said pad-like member,
   (e) a flexible secondary strap having a length less than the length of said one flexible strap, with one end portion thereof carried by said pad-like member adjacent one longitudinal side of said resilient catheter gripping member,
   (f) a retainer member carried by said pad-like member adjacent the other longitudinal side of said resilient catheter gripping member and having a longitudinally extending opening therethrough for receiving the other end portion of said flexible secondary strap with said other end portion of said flexible secondary strap extending over said resilient catheter gripping member to retain the catheter therein, and
   (g) connector means detachably connecting said other end portion of said flexible secondary strap to the outer surface of said one flexible strap.

3. A device for securing a catheter or the like to a leg of a person comprising:
   (a) a supporting pad-like member adapted to extend alongside and contact said leg of a person,
   (b) at least one flexible strap secured to said pad-like member adjacent one end portion thereof and extending laterally therefrom in position to encircle said leg of the person,
   (c) means detachably connecting said strap about said leg of the person,
   (d) means carried by said one end portion of said pad-like member for detachably connecting a catheter thereto and restraining longitudinal movement thereof,
   (e) a pair of additional flexible straps secured to and extending laterally from the other end portion of said pad-like member in position to encircle said leg of the person with connector means detachably connecting end portions of said additional straps about said leg of the person with said additional straps being laterally spaced from each other to receive said catheter therebetween,
   (f) at least one retainer element carried by said other end portion of said pad-like member in position to extend alongside one side of said catheter with said retainer element having an opening therethrough,
   (g) a secondary strap secured at one end to said pad-like member at the opposite side of said catheter from said retainer element with the other end of said secondary strap adapted to extend over said catheter and through said opening, and
   (h) connector means detachably connecting said other end of said flexible secondary strap to one of said additional flexible straps of said pair of additional flexible straps.

4. A device for securing a catheter or the like to a leg of a person comprising:
   (a) a supporting pad-like member adapted to extend alongside and contact said leg of a person,
   (b) at least one flexible strap secured to said pad-like member adjacent one end portion thereof and extending laterally therefrom in position to encircle said leg of the person,
   (c) means detachably connecting said strap about said leg of the person,
   (d) means carried by said one end portion of said pad-like member for detachably connecting a catheter thereto and restraining longitudinal movement thereof,
   (e) a pair of additional flexible straps secured to and extending laterally from the other end portion of said pad-like member in position to encircle said leg of the person with connector means detachably connecting end portions of said additional straps about said leg of the person, (f) a pair of spaced apart retainer elements carried by said other end portion of said pad-like member in position for said catheter to extend therebetween and with said retainer elements having longitudinally extending openings therethrough, (g) a flexible secondary straps having one end portion secured to said pad-like member and with its other end portion extending over said catheter and through each said longitudinally extending opening in said retainer elements, and (h) connector means detachably connecting said other end portion of said flexible secondary strap to one of said additional flexible straps of said pair of additional flexible straps.

* * * * *